(12) United States Patent
Juan Jesús et al.

(10) Patent No.: US 7,956,039 B2
(45) Date of Patent: Jun. 7, 2011

(54) USE OF AMYGDALIN ANALOGUES FOR THE TREATMENT OF PSORIASIS

(75) Inventors: Pérez Gonzáles Juan Jesús, Barcelona (ES); Amadeu Llebaria Soldevilla, Esplugues de Llobregat (ES); Carmen Lagunas Arnal, Esplugues de Llobregat (ES); Andrés Fernández Garcia, Esplugues de Llobregat (ES)

(73) Assignee: Universitat Politècnica De Catalunya, Barcelona (ES)

( * ) Notice: Subject to any disclaimer, the term of this patent is extended or adjusted under 35 U.S.C. 154(b) by 295 days.

(21) Appl. No.: 11/754,917

(22) Filed: May 29, 2007

(65) Prior Publication Data

US 2011/0028410 A9   Feb. 3, 2011

Related U.S. Application Data

(63) Continuation of application No. PCT/ES2005/000641, filed on Nov. 25, 2005.

(30) Foreign Application Priority Data

Nov. 29, 2004  (ES) .................................. 200402912

(51) Int. Cl.
*A61K 31/7034* (2006.01)
*C07H 15/18* (2006.01)
(52) U.S. Cl. ........................... 514/25; 536/4.1; 536/18.4
(58) Field of Classification Search .................. None
See application file for complete search history.

(56) References Cited

FOREIGN PATENT DOCUMENTS

JP  54098339  8/1979
JP  2003113088  4/2003

OTHER PUBLICATIONS

Fukuda et al., "Anti-tumor Promoting Effect of Glycosides from *Prunus persica* Seeds" Biol. Pharm. Bull. (2003) vol. 26 No. 2, pp. 271-273.*
Prieto et al., "Pharmacological approach to the pro- and anti-inflammatory effects of *Ranunculus sceleratus* L." Journal of Ethnopharmacology (2003) vol. 89 pp. 131-137.*
Yamazaki et al., "XPA Gene-Deficient, SCF-Transgenic Mice with Epidermal Melanin Are Resistant to UV-Induced Carcinogenesis" Journal of Investigative Dermatology (2004) vol. 123, pp. 220-228.*
Giner et al., "Anti-inflammatory glycoterpenoids from *Scrophularia auriculata*" European Journal of Pharmacology (2000) vol. 389, pp. 243-252.*
Baroni et al., "Immunomodulatory effects of a set of amygdalin analogues on human keratinocyte cells" Experimental Dermatology (2005) vol. 14 No. 11 pp. 854-859.*
Yoon et al., "Enzymatic synthesis of two salicin analogues by reaction of salicyl alcohol with *Bacillus macerans* cyclomaltodextrin glucanyltransferase and *Leuconostoc mesenteroides* B-742CB dextransucrase" Carbohydrate Research (2004) vol. 339 pp. 1517-1529.*
Heilman et al., "Radical Scavenger Activity of Phenylethanoid Glycosides in FMLP Stimulated Human Polymorphonuclear Leukocytes: Structure-Activity Relationships" Planta Medica (2000) vol. 66 pp. 746-748.*
E. M. Faber et al., "Peptide T Improves Psoriasis when Infused into Lesions in Nanogram Amounts", Proc. Natl. Acad. Sci., J Am Acad Dermatol 1991, vol. 25, p. 658.
T. Talme et al., "Histopathological and Immunohistochemical Changes in Psoriatic Skin during Peptide T Treatment", Proc. Natl. Acad. Sci., Arch Dermatol 1995, vol. 287, p. 553.
M. Marastoni et al., "Structure-Activity Relationships of Cyclics and Linear Peptide T Analogues", Int. J. Pept. Protein Res. 1993, vol. 41, pp. 447-454.
N.B. Centeno et al., "A Proposed Bioactive Conformation of Peptide T", J. Comp.-Aided Mol. Design 1998, vol. 12, p. 7-14.
O. Llorens et al., "A Proposed Bioactive Form of Peptide T and the Design of Peptidomimetics", Lett. Pept. Sci. 1998, vol. 5, pp. 179-182.
O. Llorens et al., "Amygdalin Binds to the CD4 Receptor as Suggested From Molecular Modeling Studies", Bioorg. Med. Chem. Lett. 1998, vol. 8, pp. 781-786.
C. Bliard et al., "Amygdalin as Building Block in Oligosaccharide Synthesis", Tetrahedron Lett. 1993, vol. 34., No. 32, 5083-5084.
H. Gross et al., "Dichloromethyl-Methylether as a Reagent for Organic Synthesis and Carbohydrate Chemistry", Zeitschrift für Chemie, 18 (1978) 201-210.
I. Farkas et al., "Selective Cleavage of Glycosides .5. Cleavage of Hepta-O-Acetylamygdalin by Means of Dichloromethyl Methyl-Ether", Annalen der Chemie-Justus Liebig (3): 440-449 1976.

(Continued)

*Primary Examiner* — Eric S Olson
(74) *Attorney, Agent, or Firm* — Peter B. Scull; K. Kalan; Berenbaum Weinshienk PC

(57) ABSTRACT

The compounds of formula (I), wherein n is an integer from 0 to 4; R1 is a radical selected from the group consisting of H, $CH_3$, $CH_2$-$CH_3$, $C(CH_3)_3$, COOH, $CONH_2$ and C≡CH; R2, R3, R4 and R5 are radicals independently selected from the group consisting of H, F, Cl, Br, ($C_1$-$C_3$)-alkoxyl and ($C_1$-$C_4$)-alkyl; and R6 is a radical selected from the group consisting of H, F, Cl, Br, ($C_1$-$C_3$)-alkoxyl, ($C_1$-$C_4$)-alkyl, R7, CH═CH—R7 and O—$CH_2$—R7; wherein R7 is phenyl or phenyl mono- or independently di-substituted with F, Cl, Br, ($C_1$-$C_3$)-alkoxyl or ($C_1$-$C_4$)-alkyl, exhibit a similar chemotactic index to that of amygdalin (natural product whose chemotaxis profile is similar to that of peptide T) and, consequently, are useful for treating inflammatory and/or allergic dermatophathies, such as psoriasis, and are especially much less toxic than amygdalin.

(I)

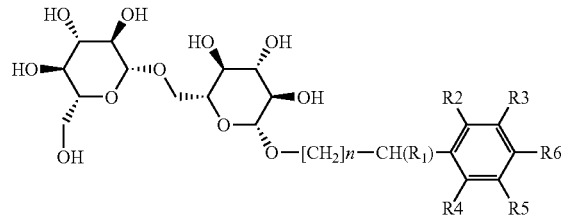

22 Claims, No Drawings

OTHER PUBLICATIONS

M. Bergmann et al., Gentiobial and the Ring Structure of Glucans (Part 13, on the Reduction Products of Unsaturated Sugars), Chem. Ber., 62 (1929) 2783-2788.

T. Ziegler et al., "Preparation of Some Amygdalin-Derived Gentiobiosyl Donors and Acceptors for Oligosaccharide Synthesis", Institut fur Organische Chemie and Isotopenforschung der Universitat Stuttgart, Pfaffenwaldring 55., J. Carbohydrate Chem., 10(5), 313-631 (1991).

MA, Seung-Jin et al., "Substrate Specificity of β-Primeverosidase, A key Enzyme in Aroma Formation during Oolong Tea and Black Tea Manufacturing", Institute for Chemical Research, Kyoto University., Bioscience, Biotechnology and Biochemistry, 2001, vol. 65, No. 12, 2719-2729.

Hirata, Toshifumi et al., "Diastereoselective Formation of Disaccharides from (RS)-1-phenylethanol by Cultured Cells of *Catharanthus roseus*"., Bulletin of the Chemical Society of Japan, 2001, vol. 74, No. 3 (Abstract).

Smith D. et al., "Preparative and Analytical Separation of Amygdalin and Related Compounds in Injectables and Tablets by Reversed-phase HPLC and the Effect of Temperature on the Separation", Journal of Chromatographic Science, 1984, vol. 22, No. 3 (Abstract).

Araya, E. et al., "Sythesis and Evaluation of Diverse Analogs of Amygdalin as Potential Peptidomimetics of Peptide T", Bioorganic & Medicinal Chemistry Letters, vol. 15, No. 5., 2005.

International Search Report and the Written Opinion corresponding to PCT/ES2005/000641, (2005).

* cited by examiner

USE OF AMYGDALIN ANALOGUES FOR THE TREATMENT OF PSORIASIS

CROSS REFERENCE TO RELATED APPLICATIONS

The present application is a 35 USC §120 continuation of PCT Application Number PCT/ES2005/000641, filed Nov. 25, 2005, which claims priority from the Spanish application no. P200402912, filed Nov. 29, 2004, entitled "USE OF AMYGDALIN ANALOGUES FOR THE TREATMENT OF PSORIASIS".

The present disclosure relates to the field of therapy and prophylaxis of psoriasis and other inflammatory and/or allergic dermopathies.

BACKGROUND

Inflammatory or allergic dermopathies may be a cause of physical and psychological problems for human beings and animals. For some of these diseases, such as psoriasis, there is no cure yet. Psoriasis is a chronic and recurrent disease. The cause of the accelerated cell growth of psoriasis is unknown, but immune mechanisms are thought to play an important role.

Peptide T is an octapeptide of sequence ASTTTNYT corresponding to a gp120 protein sequence segment of the human immunodeficiency virus. The analysis of its pharmacological profile shows that peptide T is effective in the treatment of psoriasis (cf. E. M. Faber et al., *Proc. Natl. Acad. Sci.* 1991, vol. 25, p. 658; T. Talme et al., *Proc. Natl. Acad. Sci.* 1995, vol. 287, p. 553). However, the use of peptide T as a medication is not advisable because of its low absorption, metabolic instability and immunogenic effects. As there is not yet a completely satisfactory treatment for psoriasis, it is of great interest to develop new antipsoriasis drugs.

From structure-activity studies based on the chemotactic properties of peptide T analogues (cf. M. Marastoni et al., *Int. J. Pept. Proetin Res.* 1993, vol. 41, pp. 441-454), a model of the bioactive conformation of peptide T was proposed (cf. N. B. Centeno et al., *J. Comp.-Aided Mol. Design* 1998, vol. 12, p. 7-14). In addition, this study has led to define a pharmacophore as well as its required positions for a good chemotactic activity of monocytes (cf. O. Llorens et al., Left. Pent. Sci. 1998, vol. 5, pp. 179-182). This pharmacophore was later used for in silico assays of different databases for compounds, which led to the natural product amygdalin (VII) as peptidomimetic of peptide T. Subsequent chemotaxis studies have demonstrated that amygdalin (VII) exhibits a chemotactic profile similar to that of peptide T and, consequently, a presumable similar antipsoriatic activity (cf. O. Llorens et al., *Bioorg. Med. Chem. Left.* 1998, vol. 8, pp. 781-786). Nevertheless, amygdalin (VII) is a natural product having a toxic profile. Its toxicity is known to be due to the release of cyanide ions in vivo.

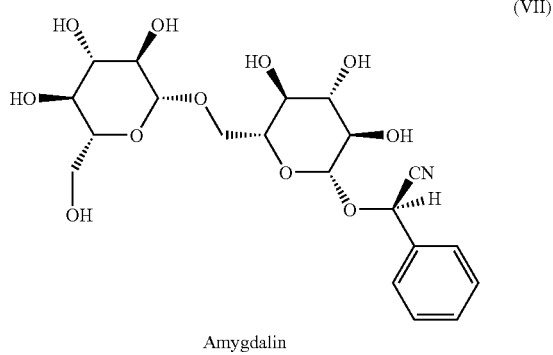

Amygdalin

DESCRIPTION SUMMARY

Disclosed here is a finding that a group of structural analogue compounds of amygdalin possess a chemotactic profile similar to that of amygdalin, which makes them be potentially useful for the prophylactic and/or curative treatment of inflammatory and/or allergic dermopathies and, particularly, for the treatment of psoriasis. Nothing in the art suggests that the compounds of formula (I) (set forth below) have the activity associated with that which is presently disclosed.

An aspect hereof relates to the use of a compound of formula (I) or its enantiomers or the mixtures thereof, or pharmaceutically acceptable salts thereof, or pharmaceutically acceptable solvates thereof, wherein n is an integer from 0 to 4; R1 is a radical selected from the group consisting of H, $CH_3$, $CH_2$-$CH_3$, $C(CH_3)_3$, COOH, $CONH_2$ and C≡CH; R2, R3, R4 and R5 are radicals independently selected from the group consisting of H, F, Cl, Br, ($C_1$-$C_3$)-alkoxyl and ($C_1$-$C_4$)-alkyl; and R6 is a radical selected from the group consisting of H, F, Cl, Br, ($C_1$-$C_3$)-alkoxyl, ($C_1$-$C_4$)-alkyl, R7, CH=CH-R7 and O-$CH_2$-R7; wherein R7 is phenyl or phenyl mono- or independently di-substituted with F, Cl, Br, ($C_1$-$C_3$)-alkoxyl or ($C_1$-$C_4$)-alkyl. Such compounds may be used for the prophylactic and/or curative treatment of an inflammatory and/or allergic dermopathy, particularly psoriasis, and/or used in the preparation of a medicament thereof. Moreover, the present disclosure also relates to a prophylactic and/or curative method for treating a patient suffering from an inflammatory and/or allergic dermopathy, particularly psoriasis, which may include administering (particularly in some implementations by oral, parenteral or topical route) a pharmaceutically effective amount of a compound of formula (I) or its enantiomers or the mixtures thereof, or their pharmaceutically acceptable salts, or their pharmaceutically acceptable solvates, together with pharmaceutically acceptable excipients or carriers. An advantage of the compounds of formula (I) over amygdalin may lie on a much lower toxicity.

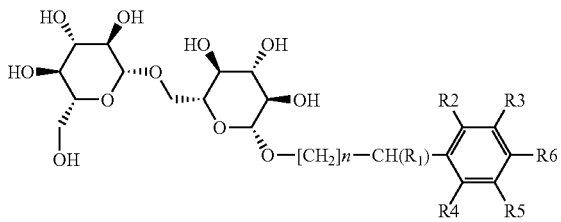

In a preferred implementation here, n is an integer from 0 and 2. Also preferred is the use of compounds (I) wherein R2, R3, R4 and R5 are radicals independently selected from the group consisting of H, F, Cl, Br, methoxyl and methyl; and R6 is a radical selected from the group consisting of H, F, Cl, Br, methoxyl, methyl, 2-phenylvinyl and phenyl. And it is especially preferred the use of the following particular compounds, the preparation of which is described in the examples disclosed herein:

4-methoxybenzyl 6-O-(β-D-glucopyranosyl)-β-D-glucopyranoside;
benzyl-6-O-(β-D-glucopyranosyl)-β-D-glucopyranoside;
(1RS)-1-phenylethyl-6-O-(β-D-glucopyranosyl)-β-D-glucopiranoside;
(1RS)-1-phenylpropyl-6-O-(β-D-glucopyranosyl)-β-D-glucopyranoside;
(1 RS)-1-phenyl-2,2-dimethylpropyl-6-O-(β-D-glucopyranosyl)-β-D-glucopyranoside;

(2R)-(6-O-(β-D-glucopyranosyl)-β-D-glucopyranosyloxy)phenylacetic acid;

(2R)-2-[(6-O-(β-D-glucopyranosyl)-β-D-glucopyranosyloxy]phenylacetamide;

(1RS)-1-phenyl-2-propynyl-6-O-(β-D-glucopyranosyl)-β-D-glucopyranoside;

2-bromobenzyl-6-O-(β-D-glucopyranosyl)-β-D-glucopyranoside;

2-chlorobenzyl 6-O-(β-D-glucopyranosyl)-β-D-glucopyranoside;

2,4-dimethoxybenzyl 6-O-(β-D-glucopyranosyl)-β-D-glucopyranoside;

2-(2-chloro-6-fluorophenyl)ethyl 6-O-(β-D-glucopyranosyl)-β-D-glucopyranoside;

(Z)-4-stilbenemethyl [6-O-(β-D-glucopyranosyl)-D-glucopyranoside];

4-biphenylmethyl 6-O-(β-D-glucopyranosyl)-β-D-glucopyranoside;

4-ethoxybenzyl 6-O-(β-D-glucopyranosyl)-β-D-glucopyranoside;

4-t-butylbenzyl 6-O-(β-D-glucopyranosyl)-β-D-glucopyranoside; and 2-phenylethyl-6-O-(β-D-glucopyranosyl)-β-D-glucopyranoside.

The compounds of formula (I) may be obtained by deprotecting the respective heptaacetylated intermediates (II), e.g., by hydrolysis, preferably by treatment with sodium methoxide in methanol at reflux temperature.

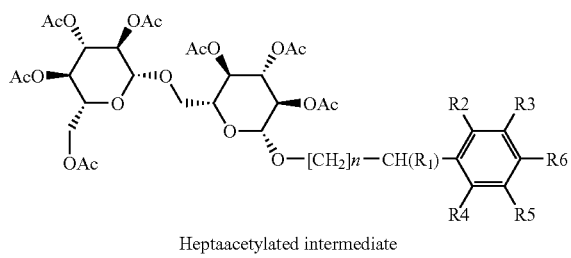

Heptaacetylated intermediate (II)

Heptaacetylated intermediates (II) may be obtained by glycosidation of respective alcohols of formula (III) with the trichloroacetimidate intermediate (IV), e.g., in dichloromethane at low temperature and with a catalytic amount of $BF_3 \cdot OEt_2$.

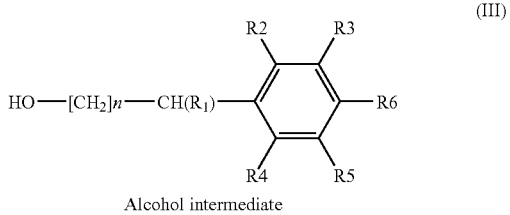

Alcohol intermediate (III)

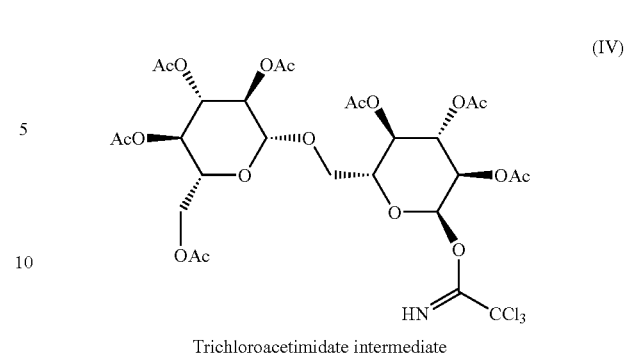

Trichloroacetimidate intermediate (IV)

The acetimidate intermediate (IV) may be obtained from the alcohol intermediate (V), e.g., by reaction with trichloroacetonitrile, as illustrated in the examples.

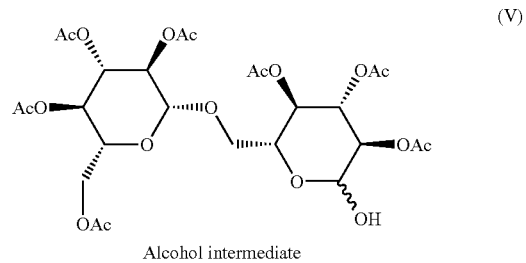

Alcohol intermediate (V)

The alcohol intermediate (V), already known in chemical literature, may be obtained by catalytic hydrogenation, preferably with $Pd(OH)_2$ as catalyst, of heptaacetylamygdalin (VI). This latter, already known in the literature, may be obtained by acetylation of amygdalin (VII), as illustrated in the examples.

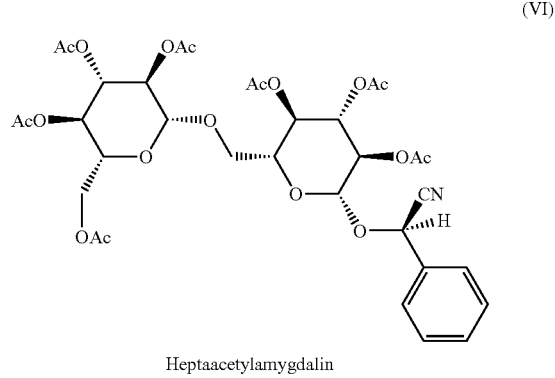

Heptaacetylamygdalin (VI)

As illustrated by the chemotaxis study in the examples, the compounds of formula (I) have a similar profile to that of amygdalin and, therefore, a potential activity against dermopathies, such as psoriasis.

It is also an aspect of the present disclosure to provide novel compounds of formula (I), their enantiomers or the mixtures thereof, or pharmaceutically acceptable salts thereof, or pharmaceutically acceptable solvates thereof wherein n is an integer from 0 to 4; R1 is a radical selected from the group consisting of H, $CH_3$, $CH_2$-$CH_3$, $C(CH_3)_3$, COOH, $CONH_2$ and C≡CH; R2, R3, R4 and R5 are radicals independently selected from the group consisting of H, F, Cl, Br, $(C_1$-$C_3)$- alkoxyl and ($C_1$-$C_4$)-alkyl; and R6 is a radical selected from the group consisting of H, F, Cl, Br, ($C_1$-$C_3$)-alkoxyl, ($C_1$-$C_4$)-alkyl, R7, CH=CH-R7 and O-$CH_2$-R7; wherein R7 is phenyl or phenyl mono- or independently di-substituted with F, Cl, Br, ($C_1$-$C_3$)-alkoxyl or ($C_1$-$C_4$)-alkyl; with the proviso that the compound of formula (I) is not any of the following ones: benzyl 6-O-(β-D-glucopyranosyl)-β-D-glucopyranoside; 1-phenylethyl-6-O-(β-D-glucopyranosyl)-O-D-glucopyranoside; (6-O-(β-D-glucopyranosyl)-β-D glucopyranosyloxy)phenylacetic acid; and 2-[(6-O-(β-D-glucopyranosyl)-β-D-glucopyranosyloxy]phenylacetamide.

Other aspects, advantages and characteristics hereof will become apparent for those skilled in the art partly in the description and partly in practicing the invention. The following examples and drawings are provided as an illustration and are not intended to be limitative of the present invention.

DETAILED DESCRIPTION OF PARTICULAR IMPLEMENTATIONS

Preparation of heptaacetylamygdalin (VI) or (R)-α-[(2,3,4,6-tetra-O-acetyl-β-D-gluconyranosyl (1→6)-2,3,4-tri-O-acetyl-β-D-glucopyranosyl)oxy]phenylacetonitrile This product was described in C. Bliard et al., *Tetrahedron Lett.* 1993, 32, 5083-5084: H. Gross et al., *Ztschr Chem.*, 1978, 201; I. Farkas et al., *Liebigs Ann. Chem.*, 1976, 440. To a solution of amygdalin (9.15 g, 20.0 mmol) in dichloromethane (200 mL), a catalytic amount (0.2 g) of 4-dimethylaminopyddine was added and the mixture was kept under stirring at 0° C. Then, acetic anhydride (35 mL, 375 mmol) was slowly added and the temperature was kept at 0° C. The mixture was left to reach room temperature and stirred at this temperature for 12 h. The solvent was evaporated, the resulting residue was dissolved in AcOEt (150 mL) and the organic layer was successively washed with three volumes of water, three volumes of saturated $CuSO_4$ aqueous solution and three volumes of brine. The solution was dried over anhydrous sodium sulphate, filtered and evaporated yielding the title compound as a white solid (14.8 g, 98%). $^1$H-NMR (300 MHz, $CDCl_3$) δ(ppm): 7.43(1H, s), 5.52(1H, s), 5.25(1H, t, J=9.3), 5.10-4.96(4H, m), 4.87(1H, t, J=9.3), 4.64(1H, d, J=7.8), 4.38(1H, d, J=7.8), 4.25(1H, dd, J=4.8, J=12.4), 4.08 (1H, dd, J=2,1, J=12.4), 3.82(1H, m), 3.71(1H, m), 3.60(2H, m), 2.10-1.90(21H, m); $^{13}$C-NMR (75 MHz, $CDCl_3$) δ(ppm): 170.45, 170.06, 170.02, 169.51, 169.47, 169.42, 168.93,132.09, 130.38, 129.24, 127.63, 117.12, 100.41, 97.78, 73.64, 72.48, 72.35, 71.83, 71.28, 70.80, 68.62, 68.09, 67.83, 67.67, 61.68, 20.90-20.60 (7C).

Preparation of Intermediate (V) or 2,3,4,6tetra-O-acetyl-β-D-glucopyranosyl (1→6)-2,3, 4-tri-O-acetyl-β-D-glucopyranoside This product was described in M. Bergmann et al, *Chem. Ber.* 1929, 62, 2783. Following an adaptation of the process described for the transformation of hepta-O-benzoylamygdalin into hepta-O-benzoyl-D-gentiobiose (cf. T. Ziegler et al, *Carbohydr Chem.* 1991, 10, 813-831), a suspension of the heptaacetylamygdalin (VI) obtained in the previous step (9.0 g, 12 mmol) and 20% Pd(OH)$_2$ on charcoal (3.6 g) in a mixture of toluene-acetone (3:2 v:v, 500 mL) was subjected to hydrogenation at room temperature under 1.0 bar pressure until the control by thin-layer chromatography indicated the complete conversion of amygdalin into a lower mobility product (3-5 h). The mixture was filtered and the filtrate was evaporated. The obtained residue was dissolved in ethyl acetate (200 mL) and successively washed with a volume of 1N hydrochloric acid and brine. The organic layer was dried over anhydrous sodium sulphate, filtered and the filtrate was evaporated to dryness. The resulting residue was recrystallized from ethanol to give 6.80 g (86%) of the title compound as a white solid. $^1$H-NMR (300 MHz, $CDCl_3$) δ(ppm): 5.50 (1H, dd, J=9.6, J=10.2), 5.19(1H, t, J=9.6), 5.07(1H, t, J=9.6), 4.94(1H, dd, J=8.1, J=9.6), 4.88-4.81(2H, m), 4.55(1H, d, J=8.0), 4.26-4.12(2H, m), 3.85-3.80(1H, m), 3.72-3.65(1H, m), 3.63-3.56(2H). $^{13}$C-NMR (75 MHz, $CDCl_3$) δ(ppm): 170.27, 170.17, 170.09, 169.70, 169.39, 169.36, 169.21, 101.05, 89.95, 72.55, 71.96, 71.18, 71.00, 69.85, 69.13, 68.76, 68.07, 67.96, 62.51, 61.60, 20.50-20.30(7 C).

Preparation of trichloroacetimidate Intermediate (IV) or O-(2,3,4,6-tetra-acetyl-β-D-glucopyranosyl (1→6)-2, 3, 4-tri-O-acetyl-β-D-glucopyranosyl) trichloroacetimidate A catalytic amount of 60% NaH in mineral oil (approx. 0.025 mmol) was added to a solution of intermediate (V) (500 mg, 0.8 mmol) and trichloroacetonitrile (0.5 mL, 5.0 mmol) in dichloromethane (20 mL) and the mixture was stirred at room temperature until observing -by thin-layer chromatography—the complete disappearance of starting material in the reaction mixture and its conversion into a new product with higher mobility under thin-layer chromatography (usually from 15 to 30 min). The mixture was evaporated to dryness and the resulting residue (essentially constituted by crude trichloroacetimidate) was immediately used without further purification in the following glycosylation reaction.

Examples of compounds (I) described hereinafter were prepared using the trichloroacetimidate intermediate (IV) and the corresponding alcohols (III) to give the respective heptaacetylated intermediates (II), which by hydrolysis yielded said compounds (I).

REFERENCE EXAMPLE 1

Preparation of Compound (I-1) or 4-methoxybenzyl 6-O-(β-D-glucopyranosyl)-β-D-Glucopyranoside (n=0; R1=R2=R3=R4=R5=H; R6=$OCH_3$)

a) Preparation of heptaacetylated intermediate (II-1) or O-4-methoxybenzyl-6-O-(β-D-glucopyranosyl)-O-D-glucopyranoside Under a dry nitrogen atmosphere, a solution of 4-methoxybenzyl alcohol (III-1) (323.1 mg, 2.34 mmol) in 15 mL of dichloromethane was slowly added to a solution of trichloroacetimidate intermediate (IV) (500 mg) in 10 mL of anhydrous dichloromethane by keeping the temperature below −50° C. A catalytic amount of $BF_3.OEt_2$ (0.12 mol-eq) was added and stirred at this temperature for 15 min. Then the cooling bath was removed, and the temperature of the reaction mixture was allowed to rise slowly until reaching room temperature. After stirring for 3 hours, the reaction was stopped by adding 20 mL of saturated $NH_4Cl$ aqueous solution and extracted with three portions of 20 mL of AcOEt. The combined organic layers were washed with brine, dried over $Na_2SO_4$, filtered and the filtrate was evaporated to dryness yielding a solid brown residue, which was purified by flash chromatography (hexane/AcOEt 9:1) to give, by combination and evaporation of the desired fractions, 119.5 mg (0.16 mmol, 20% yield calculated from hepta-O-acetylgentiobiose) of the title compound.

b) Preparation of compound (I-1) by deprotection of the heptaacetylated intermediate (II-1)

The obtained heptaacetyl-O-4-methoxybenzyl-6-O-(β-D-glucopyranosyl)-β-D-glucopyranoside derivative (119.5 mg, 0.16 mmol) was dissolved in 5 mL of MeOH and 25 μL of a freshly prepared 0.1M solution of NaOMe in MeOH were added. The mixture was heated to reflux under stirring until disappearance of starting material, then cooled and evaporated to dryness to give 68.5 mg (0.15 mmol, 94%) of the title compound as a colourless, hygroscopic solid, purity being higher than 95% by HPLC. $^1$H-NMR (300 MHz, CD$_3$OD) δ(ppm): 7.34(2H, d, J=9.0 Hz), 6.89(2H, d, J=9.0 Hz), 4.88 (1H, d, J=11.8 Hz), 4.59(1H, d, J=11.8Hz), 4.42 (1H, d, J=7.5), 4.34(1H, d), 4.18(1H, dd, J=1.5, J=11.4), 3.91-3.80 (2H, m), 3.78(3H, s) 3.65-3.58(1H, m), 3.45-3.22(7H, m). $^{13}$C-NMR (75 MHz, CD$_3$OD) δ(ppm): 160.90,130.99,130.90, 114.64, 104.87, 103.07, 78.02, 77.93, 77.13, 75.11, 75.03, 71.70, 69.74, 62.72, 55.66(2C). IR (KBr), ν$_{max}$(cm$^{-1}$): 3500-3100, 2970-2940, 1635,1620,1545, 1525.

EXAMPLE 2

Preparation of Compound (I-2) or benzyl 6-O-(β-D-glucopyranosyl)4-D-glycopyranoside (n=0; R1= R2 =R3 =R4 =R5 =R6 =H)

Starting from the trichloroacetimidate intermediate (IV) and reacting it with the corresponding alcohol, in the same way as in Example 1, the title compound was obtained with 22% yield. $^1$H-NMR (300 MHz, CD$_3$OD) δ(ppm): 7.45-7.26 (5H, m), 4.93(1H, d, J=12.0), 4.66(1H, d, J=12.0), 4.42(1H, d, J=7.8), 4.37(1H, d, J=7,5), 4.18(1H, dd, J=1.8, J=11.7), 3.90-3.75(2H, m), 3.67(1H, dd, J=5.4, J=11.9), 3.48-3.21(8H, m). $^{13}$C-NMR (75 MHz, CD$_3$OD) δ(ppm): 139.01, 129.27, 129.20, 128.68, 104.89, 103.40, 78.04, 78.00, 79.96, 77.16, 75.10, 75.10, 71.95, 71.57, 71.55, 69.76, 62.72. IR (evaporated film), ν$_{max}$ (cm$^{-1}$): 3600-3100, 2970-2940, 1645, 1550, 1505.

EXAMPLE 3

Preparation of Compound (I-3) or (1 RS)-1-phenyl-ethyl-6-O-(β-D-glucopyranosyl)-β-D-glucopyrano-side (n=0; R1=CH$_3$; R2=R3=R4=R5=R6=H)

Starting from the trichloroacetimidate intermediate (IV) and reacting it with the corresponding alcohol, in the same way as in Example 1, the title compound was obtained with 33% yield. $^1$H-NMR (300 MHz, CD$_3$OD) δ(ppm): 7.45-7.22 (5H, m), 5.05-4.95(1H, m), 4.49-4.32(2H, m), 4.16-4.02(2H, m), 3.90-3.60(2H, m), 3.20-3.05(8H, m) 2.60-2.70(3H, m). $^{13}$C-NMR (75 MHz, CD$_3$OD) δ(ppm): 145.09, 144.08, 129.39, 129.10, 128.58, 128.23, 127.95, 127.44, 104.81, 104.79, 102.35, 78.04 (2C), 77.85, 77.85, 77.28, 77,27, 77.01, 76.18, 75.15 (2C), 75.10(2C), 71.50, 71.49, 69.62 (2C), 62.65 (2C), 24.72, 22.20. IR (evaporated film), ν$_{max}$ (cm$^{-1}$): 3600-3100, 2970-2940, 1645,1550, 1505.

EXAMPLE 4

Preparation of Compound (I-4) or (1 RS)-1-phenyl-propyl 6-O-(β-D-glucopyranosyl)-β-D-glucopyrano-side (n=0; R1=CH$_2$-CH$_3$; R2=R3=R4=R5=R6=H)

Starting from the trichloroacetirnidate intermediate (IV) and reacting it with the corresponding alcohol, in the same way as in Example 1, the title compound was obtained with 63% yield. $^1$H-NMR (300 MHz, CD$_3$OD), δ(ppm): 7.45-7.22 (5H, m), 5.05-4.95(1H, m), 4.51-4.32(2H, m), 4.16-4.02(2H, m), 3.90-3.60(2H, m), 3.20-3.05(8H, m) 2.60-2.70(2H, m), 1.04(t, 3H). $^{13}$C-NMR (75 MHz CD$_3$OD) δ(ppm): 144.97, 144.21, 129.39, 129.12, 128.43, 128.32, 128.11, 127.44, 104.81, 104.79, 102.35, 78.14, 78.11, 78.08, 77.95, 77.48, 77.33, 77.11, 76.38, 75.13 (2C), 75.10(2C), 71.50, 71.49, 69.62 (2C), 62.65 (2C), 24.72, 22.40, 14.34. IR (evaporated film), ν$_{max}$ (cm$^{-1}$): 3600-3100, 2970-2940, 1645, 1550, 1510.

EXAMPLE 5

Preparation of Compound (I-5) or (1RS) 1-phenyl-2,2-dimethylpropyl-6-O-(β-D-glucopyranosyl)-β-D-glucopyranoside (n=0; R1=C(CH$_3$)$_3$; R2=R3=R4=R5=R6=H)

Starting from the trichloroacetimidate intermediate (IV) and reacting it with the corresponding alcohol, in the same way as in Example 1, the title compound was obtained with 60% yield as a mixture of epimers 3:2 in the benzyl carbon by NMR. $^1$H-NMR (300 MHz, CD$_3$OD), δ(ppm): 7.42-7.19(5H, m), 4.66(1H, s), 4.57(1H, d, J=7.8), 4.39-4.34(2H, m), 4.11-3.99(4H, m), 3.90-3.76(4H), 3.70-3.56(2H, m), 3.31-3.26 (6H, m), 0.96(9H, s). $^{13}$C-NMR (75 MHz, CD$_3$OD) δ(ppm): 142.04, 140.12, 130.41, 129.66, 128.27, 127.99, 127.87, 105.46, 104.94, 104.52, 100.97, 91.11, 86.63, 78.06, 77.91, 77.59, 77.46, 77.33, 75.96, 75.15, 71.95, 71.56, 71.40, 69.71, 69.54, 62.68, 62.50, 37.07, 35.99, 26.93, 26.71. IR (evaporated film), ν$_{max}$ (cm$^{-1}$): 3600-3100, 2970-2940, 1645,1510.

EXAMPLE 6

Preparation of Compound (I-6) or (2R) (6-O-(β-D-glucopyranosyl)-β-D-glucopyranosyloxy)-phenylacetic acid (n=0; R1=COOH; R2=R3=R4=R5=R6=H)

Starting from the trichloroacetimidate intermediate (IV) and reacting it with the corresponding alcohol, in the same way as in Example 1, the title compound was obtained with 34% yield. $^1$H-NMR (300 MHz, CD$_3$OD), δ(ppm): 7.60-7.25 (5H, m), 5.29(1H, s), 4.50(1H, d, J=7.5), 4.33(1H, d, J=7.5), 4.20-4.08(2H, m), 3.91-3.65(4H, m), 3.35-3.16(6H, m), $^{13}$C-NMR (75 MHz, CD$_3$OD) δ(ppm): 173.53, 137.80, 129.63, 129.44, 128.99, 128.57, 104.94, 103.11, 101.23, 79.04, 77.93, 77.74, 77.32, 77.36, 75.15, 71.49, 71.37, 69.87, 62.65.

EXAMPLE 7

Preparation of Compound (I-7) or (2R) 2-[(6-O-(β-D-glucopyranosyl)-β-D-glucopyranosyloxy]phenylacetamide (n=0; R1=CONH$_2$; R2=R3=R4=R5=R6=H)

Starting from the trichloroacetimidate intermediate (IV) and reacting it with the corresponding alcohol, in the same way as in Example 1, the title compound was obtained with 22% yield. $^1$H-NMR (300 MHz, CD$_3$OD), δ(ppm): 7.60-7.25 (5H, m), 5.54(1H, s) 4.45(1H, d, J=7.8), 4.38(1H, d, J=7.6), 4.20-4.08(1H, m), 3.91-3.65(4H, m), 3.35-3.04(6H, m), $^{13}$C-NMR (75 MHz, CD$_3$OD) δ(ppm): 176.53, 138.76, 129.31, 128.58, 104.95, 103.40, 81.23, 77.84, 77.41, 75.11, 74.99, 71.38, 69.92, 62.58.

EXAMPLE 8

Preparation of Compound (I-8) or (1 RS) 1-phenyl-2-propynyl-6-O-(β-D-Glucopyranosyl)-β-D-glucopyranoside (n=0; R1=CH; R2=R3=R4=R5=R6=H)

Starting from the trichloroacetimidate intermediate (IV) and reacting it with the corresponding alcohol, in the same way as in Example 1, the title compound was obtained with 55% yield as a mixture of epimers 1:1 in the benzyl carbon. $^1$H-NMR (300 MHz, CD$_3$OD), δ(ppm): 7.60-7.57(2H, m), 7.40-7.31(3H, m), 5.75(0.5H, bs), 5.67(0.5H, bs), 4.80(1H, d, J=7.8), 4.51(0.5 H, d, J=7.8), 4.42(0.5 H, d, J=7.6), 4.23-4.14 (2H, m), 3.91-3.65(4H, m), 3.35-3.26(6H, m), 3.13(0.5 H, d, J=2.4), 3.08(0.5 H, d, J=1.6). $^{13}$C-NMR (75 MHz, CD$_3$OD) δ(ppm): 139.47, 139.27, 129.64, 129.52, 129.41, 129.27, 129.07, 128.76, 104.91, 104.80, 101.23, 101.10, 83.56, 81.95, 77.93, 77.81, 77.77, 77.36, 77.18, 76,44, 75.15, 75.03, 74.90, 74.74, 71.55, 71.44, 70.10, 69.75, 69.55, 62.67. IR (evaporated film), ν$_{max}$ (cm$^{-1}$): 3600-3100, 3080, 2970-2940, 2100, 1645, 1550, 1505.

EXAMPLE 9

Preparation of Compound (I-9) or 2-bromobenzyl-6-O-(β-D-glucopyranosyl)-β-D-glucopyranoside (n=0; R1=H; R2=Br; R3=R4=R5=R6=H)

Starting from the trichloroacetimidate intermediate (IV) and reacting it with the corresponding alcohol, in the same way as in Example 1, the title compound was obtained with 83% yield. H-NMR (300 MHz, CD$_3$OD), δ(ppm): 7.68(1H, dd, J=7.5, 1.2 Hz ,7.55(1H, d, J=7.5), 7.35(1H, t, J=7.5), 7.19(1H, td, J=7.5, 1.5 Hz), 4.95(1H, d, J=13.2), 4.76(1H, d, J=13.2), 4.45-4.39(2H, m), 4.17(1H, dd, J=1.8, J=11.6), 3.89-3.80(2H, m), 3.69-3.64(1H, m), 3.56-3.44(1H, m), 3.42-3.20 (7H, m). $^{13}$C-NMR (75 MHz, CD$_3$OD) δ(ppm): 138.55, 133.41, 130.64, 130.17, 128.55, 123.38, 104.79, 103.92, 77.98 (2C), 77.88, 77.23, 75.11(2C), 71.54, 71.40, 71.32, 69.65, 62.70. IR (evaporated film), ν$_{max}$ (Cl): 3600-3100, 2970-2940, 1645, 1550, 1505.

EXAMPLE 10

Preparation of Compound (I-10) or 2-chlorobenzyl 6-O-(β-D-gluconyranosyl)-β-D-Glucopyranoside (n=0; R1=H; R2=Cl; R3=R4=R5=R6=H)

Starting from the trichloroacetimidate intermediate (IV) and reacting it with the corresponding alcohol, in the same way as in Example 1, the title compound was obtained with 77% yield. $^1$H-NMR (300 MHz, CD$_3$OD), δ(ppm): 7.65-7.62(1 H, m), 7.34-7.20(3H, m), 4.95(1H, d, J=13.5), 4.74 (1H, d, J=13.5), 4.43(1H, d, J=7.3), 4.40(1H, d, J=7.3), 4.16 (1H, dd, J-1.9, 11.5), 3.90-3.79(2H, m), 3.68-3.63(2H, m), 3.54-3.20(7H, m). $^{13}$C-NMR (75 MHz, CD$_3$OD) δ(ppm): 136.91, 133.79, 130.64, 130.12, 129.98, 127.98, 104.81, 103.94, 77.98 (2C), 77,90, 77.20, 75.10 (2C), 71.53, 71.40, 69.70, 62.07. IR (evaporated film), ν$_{max}$ (cm$^{-1}$): 3600-3100, 2970-2950, 1645, 1540, 1510.

EXAMPLE 11

Preparation of Compound (I-11) or 2.4-dimethoxybenzyl 6-O-(β-D-glucopyranosyl)-β-D-glucopyranoside (n=0; R1=H; R2=OCH$_3$; R3=R4=R5=H; R6=OCH$_3$)

Starting from the trichloroacetimidate intermediate (IV) and reacting it with the corresponding alcohol, in the same way as in Example 1, the title compound was obtained with 13% yield. $^1$H-NMR (300 MHz, CD$_3$OD), δ(ppm): 6.88(1H, d, J=2.0), 6.75(2H, m), 4.78(1H, d, J=11.9 Hz), 4.69(1H, d, J=11.9 Hz), 4.44(1H, d, J=7.5), 4.37(1H, d, J=7.4), 4.18(1H, dd, J=1.5, 11.4), 3.91-3.80(2H, m), 3.78(3H, s), 3.72(3H, s), 3.65-3.58(1H, m), 3.45-3.20(BH, m). $^{13}$C-NMR (75 MHz, CD$_3$OD) δ(ppm): 160.90, 158.35, 130.39, 130.10, 114.63, 104.81, 104.03, 78.22, 77.53, 77.13, 75.11, 75.03, 71.70, 69.74, 66.42, 62.72, 55.13. IR (KBr), ν$_{max}$ (cm$^{-1}$): 3500-3100, 2970-2940, 1635, 1620, 1545, 1525.

EXAMPLE 12

Preparation of Compound (I-12) or 2-(2-chloro-6-fluorophenyl) ethyl 6-O-(β-D-glycopyranosyl)-β-D-glucopyranoside (n=1; R1=H; R2=F; R3=H; R4=Cl; R5=R6=H)

Starting from the trichloroacetimidate intermediate (IV) and reacting it with the corresponding alcohol, in the same way as in Example 1, the title compound was obtained with 33% yield. $^1$H-NMR (300 MHz, CD$_3$OD), δ(ppm): 7.26-7.23 (2H, m), 7.06-7.04(1H, m), 4.35(1H, d, J=7.6),4.31(1H, d, J=7.9)), 4.13(1H, dd, J=2.1, 1J=11.7), 4.02-3.94(1H, m), 3.88-3.73(3H, m), 3.68-3.55(3H, m), 3.48-3.26(6H, m), 3.21-3.15(2H, m). IR (evaporated film), ν$_{max}$ (cm$^{-1}$): 3600-3100, 2970-2940, 1650, 1550, 1510.

EXAMPLE 13

Preparation of Compound (I-13) or (Z)-4-stilbenemethyl [6-O-(β-D-glucopyranosyl)-D-glucopyranoside] (n=0; R1=R2=R3=R4=R5=H; R6=2-phenylvinyl)

Starting from the trichloroacetimidate intermediate (IV) and reacting it with the corresponding alcohol, in the same way as in Example 1, the title compound was obtained with 93% yield. $^1$H-NMR (300 MHz, CD$_3$OD), δ(ppm): 7.56-7.17 (11H, m), 4.91(1H, d, J=12.3),4.68(1H, d, J=12.3), 4.44-4.38 (2H, m), 4.21(1H, dd, J=8.7, 2.1), 3.91-3.81(3H, m), 3.50-3.30(8H, m). $^{13}$C-NMR (75 MHz, CD$_3$OD) δ(ppm): 142.00, 137.05, 135.48, 128.49, 128.27, 127.80, 127.33, 126.80, 126.23, 126.13, 104.58, 103.77, 77.38, 77.34, 75.25, 72.01, 71.60, 71.62, 69.46, 62.67.

EXAMPLE 14

Preparation of Compound (I-14) or 4-biphenylmethyl 6-O-(β-D-glucopyranosyl)-β-D-glucopyranoside (n=0; R1=R2=R3=R4=R5=H; R6=phenyl)

Starting from the trichloroacetimidate intermediate (IV) and reacting it with the corresponding alcohol, in the same way as in Example 1, the title compound was obtained with 73% yield. $^1$H-NMR (300 MHz, CD$_3$OD), δ(ppm): 7.63-7.28 (9H, m), 4.97(1H, d, J$_{AB}$=12.0), 4.72(1H, d, J$_{AB}$=12.0), 4.43 (1H, d, JA=7.8), 4.40(1H, d, J$_{AB}$=7.60), 4.19(1H, dd, J=2.10, 11.60), 3.90-3.80(2H, m), 3.80-3.47(3H, m), 3.39-3.25(6H). $^{13}$C-NMR (75 MHz, CD$_3$OD) δ(ppm): 142.19, 141.89, 138.17, 129.85, 129.76, 128.77, 127.94, 127.88 , 104.91, 103.35, 78.03, 78.01, 77.22, 75.12 (2C), 72.03, 71.58 (2C), 71.52, 69.79, 62.74.

EXAMPLE 15

Preparation of Compound (I-15) or 4-ethoxybenzyl 6-O-(β-D-glucopyranosyl)-β-D-glucopyranoside (n=0; R1=R2=R3=R4=R5=H; R6OCH$_2$CH$_3$)

Starting from the trichloroacetimidate intermediate (IV) and reacting it with the corresponding alcohol, in the same way as in Example 1, the title compound was obtained with 77% yield. $^1$H-NMR (300 MHz, CD$_3$OD), δ(ppm): 7.28 (2H, d, J=9.2), 6.82(2H, d, J=9.2), 4.80(1H, d, J$_{AB}$=11.4), 4.54(1H, d, J$_{AB}$=11.4), 6.83(2H, d, J=9.2), 4.39(1H, d, J=7.5), 4.31(1H, d, J=7.8), 4.14(1H, dd, J=1.8, 11.7), 3.98(2H, q, J=6.9), 3.87-3.75(2H, m), 3.68-3.60(1H, m), 3.34-3.18(6H, m), 1.33(3H, t, J=6.9). $^{13}$C-NMR (75 MHz, CD$_3$OD) δ(ppm): 160.10, 130.96, 130.79, 115.21, 104.85, 103.05, 77.98, 77.92, 77.09, 75.09, 75.02, 71.69, 71.49, 69.73, 64.41, 62.70, 58.12, 15.16. IR (evaporated film), ν$_{max}$ (cm$^{-1}$): 3600-3100, 2970-2940, 1650, 1530, 1515.

EXAMPLE 16

Preparation of Compound (I-16) or 4-t-butylbenzyl 6-O-(β-D-glucopyranosyl)-β-D-glucopyranoside (n=0; R1=R2=R3=R4=R5=H; R6=C(CH$_3$)$_3$)

Starting from the trichloroacetimidate intermediate (IV) and reacting it with the corresponding alcohol, in the same way as in Example 1, the title compound was obtained with 93% yield. $^1$H-NMR (200 MHz, CD$_3$OD), δ(ppm): 7.37-7.32 (2H, m), 7.24-7.18(2H, m), 5.01(1H, d, J$_{AB}$=12.2), 4.65(1H, d, J$_{AB}$=12.2), 4.40-4.35(2H, m), 3.90-3.75(2H, m), 3.65(1H, dd, J=5.5, J=11.9), 3.38-3.22(6H, m), 1.35(9H, s). $^{13}$C-NMR (75 MHz, CD$_3$OD) δ(ppm): 126.97, 133.54, 127.41, 125.39, 104.48, 103.5, 78.02, 77.08, 75.05, 71.51, 71.63, 71.43, 69.74, 64.77, 62.70,31.29.

EXAMPLE 17:

Preparation of Compound (I-17) or 2-phenylethyl 6-O-(β-D-glucopyranosyl)-β-D-glucopyranoside (n=1; R1=R2=R3=R4=R5=R6=H)

Starting from the trichloroacetimidate intermediate (IV) and reacting it with the corresponding alcohol, in the same way as in Example 1, the title compound was obtained with 88% yield. $^1$H-NMR (300 MHz, CD$_3$OD), δ(ppm): 7.29-7.25 (5H, m), 4.36(1H, d, J=7.8), 4.31(1H, d, J=7.8), 4.17-4.03 (2H, m), 3.90-3.60(4H, m), 3.48-3.16(8H, m), 2.93(2H, t, J=8.2). $^{13}$C-NMR (75 MHz, CD$_3$OD) δ(ppm): 140.03, 130.03, 129.36, 127.20, 104.82, 104.41, 77.98, 77.96,.77.01, 75.04, 75.02, 71.88, 71.54, 71.34, 69.73, 62.71, 37.21.

Activity of Compounds (I) in Monocyte Chemotaxis Assays

Blood mononuclear cells were isolated from heparinized blood of human volunteers by Ficoll sedimentation. Chemotaxis was measured in a modified Boyden chamber using a Millipore 8 mm filter that divided the upper and lower compartments. Mononuclear cells (0.5×10$^6$) in Krebs-Ringer phosphate (KRP) buffer were placed into the upper wells. Compounds (I) were dissolved in DMSO at 10$^{-2}$ mol/L, diluted with KRP buffer containing 1 mg/mL of bovine serum albumin and tested in the bottom compartment at a final concentration ranging from 10$^{-12}$ to 10$^{-7}$ mol/L. For an accurate comparison, the results of the different analogues were expressed as chemotactic index, which is the ratio of the distance of migration towards tested attractant and the distance towards the buffer. Migration in the presence of buffer was only 35±2 mm (mean±SEM). Maximum migration for CHO-Met-Leu-Phe-OH (FMLP) occurred at 10$^{-8}$ mol/L and was 68 mm±3 in these experiments (chemotactic index 1.94±0.03). CD4 receptor binding for the test analogues was confirmed by blocking their chemotactic effects using low concentrations (0.1-0.2 mg/mL) of OKT4, a specific monoclonal antibody for CD4 molecules. In this test, migration response was not influenced by OKT4. The results are shown in the below table.

TABLE

Maximum values of chemotactic index and values of respective concentrations [A] for various compounds (I)

| Compound (I) | Chemotactic index | −log[A] |
| --- | --- | --- |
| Peptide T | 1.09 | 11 |
| Amygdalin | 0.63 | 10 |
| (I-1) | 0.87 | 10 |
| (I-2) | 0.76 | 8 |
| (I-3) | 0.77 | 8 |
| (I-4) | 0.75 | 6 |
| (I-5) | 0.84 | 9 |
| (I-6) | 0.85 | 9 |
| (I-7) | 0.84 | 7 |
| (I-8) | 0.79 | 6 |
| (I-10) | 0.94 | 10 |
| (I-11) | 0.84 | 10 |
| (I-17) | 0.70 | 9 |

The invention claimed is:

1. A method for treating a patient suffering from psoriasis, comprising administering to the patient a pharmaceutically effective amount of one or more of a compound of formula (I) or its enantiomers or the mixtures thereof, or their pharmaceutically acceptable salts, or their pharmaceutically acceptable solvates, together with pharmaceutically acceptable excipients or carriers;

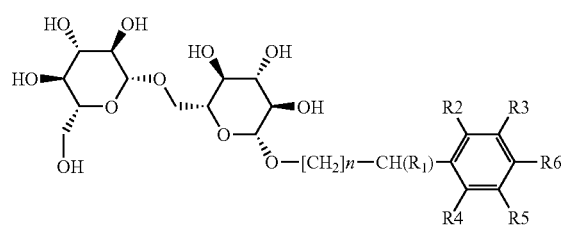

(I)

wherein n is an is an integer from 0 to 4; R1 is a radical selected from the group consisting of H, CH$_3$, CH$_2$-CH$_3$, C(CH$_3$)$_3$, COOH, CONH$_2$ and C≡CH; R2, R3, R4 [y] and R5 are radicals independently selected from the group consisting of H, F, Cl, Br, (C$_1$-C$_3$)-alkoxyl and (C$_1$-C$_4$)-alkyl; and R6 is a radical selected from the group consisting of H, F, Cl, Br, (C$_1$-C$_3$)-alkoxyl, (C$_1$-C$_4$)-alkyl, R7, CH=CH—R7 and O—CH$_2$—R7; and wherein R7 is phenyl or phenyl mono- or independently di-substituted with F, Cl, Br, (C$_1$-C$_3$)-alkoxyl or (C$_1$-C$_4$)-alkyl.

2. The method according to claim 1, wherein n is an integer from 0 to 2.

3. The method according to claim 1, wherein R2, R3, R4 and R5 are radicals independently selected from the group consisting of H, F, Cl, Br, methoxyl and methyl; and R6 is a radical selected from the group consisting of H, F, Cl, Br, methoxyl, methyl, 2-phenylvinyl and phenyl.

4. The method according to claim 1, wherein the compound of formula (I) is 4-methoxybenzyl 6-O-(β-D-glucopyranosyl)-β-D-glucopyranoside.

5. The method according to claim 1, wherein the compound of formula (I) is benzyl 6-O-(β-D-glucopyranosyl)-β-D-glucopyranoside.

6. The method according to claim 1, wherein the compound of formula (I) is (1RS)-1-phenylethyl-6-O-(β-D-glucopyranosyl)-β-D-glucopyranoside.

7. The method according to claim 1, wherein the compound of formula (I) is (1RS)-1-phenylpropyl-6-O-(β-D-glucopyranosyl)-β-D-glucopyranoside.

8. The method according to claim 1, wherein the compound of formula (I) is (1RS)-1-phenyl-2,2-dimethylpropyl-6-O-(β-D-glucopyranosyl)-β-D-glucopyranoside.

9. The method according to claim 1, wherein the compound of formula (I) is (2R) (6-O-(β-D-glucopyranosyl)-β-D-glucopyranosyloxy)phenylacetic acid.

10. The method according to claim 1, wherein the compound of formula (I) is (2R)-2-[(6-O-(β-D-glucopyranosyl)-β-D-glucopyranosyloxy]phenylacetamide.

11. The method according to claim 1, wherein the compound of formula (I) is (1RS)-1-phenyl-2-propynyl-6-O-(β-D-glucopyranosyl)-β-D-glucopyranoside.

12. The method according to claim 1, wherein the compound of formula (I) is 2-bromobenzyl-6-O-(β-D-glucopyranosyl)-β-D-glucopyranoside.

13. The method according to claim 1, wherein the compound of formula (I) is 2-chlorobenzyl-6-O-(β-D-glucopyranosyl)-β-D-glucopyranoside.

14. The method according to claim 1, wherein the compound of formula (I) is 2,4-dimethoxybenzyl 6-O-(β-D-glucopyranosyl)-β-D-glucopyranoside.

15. The method according to claim 1, wherein the compound of formula (I) is 2-(2-cloro-6-fluorophenyl)ethyl 6-O-(β-D-glucopyranosyl)-β-D-glucopyranoside.

16. The method according to claim 1, wherein the compound of formula (I) is (Z)-4-stilbenemethyl [6-O-(β-D-glucopyranosyl)-D-glucopyranoside].

17. The method according to claim 1, wherein the compound of formula (I) is 4-biphenylmethyl 6-O-(β-D-glucopyranosyl)-β-D-glucopyranoside.

18. The method according to claim 1, wherein the compound of formula (I) is 4-ethoxybenzyl 6-O-(β-D-glucopyranosyl)-β-D-glucopyranoside.

19. The method according to claim 1, wherein the compound of formula (I) is 4-t-butylbenzyl 6-O-(β-D-glucopyranosyl)-β-D-glucopyranoside.

20. The method according to claim 1, wherein the compound of formula (I) is 2-phenylethyl 6-O-(β-D-glucopyranosyl)-β-D-glucopyranoside.

21. The method according to claim 1, wherein treatment is applied by oral, parenteral or topical route.

22. A method for treating a patient suffering from one or both of an inflammatory and/or allergic dermopathy, comprising administering to the patient a pharmaceutically effective amount of one or more of a compound of formula (I) or its enantiomers or the mixtures thereof, or their pharmaceutically acceptable salts, or their pharmaceutically acceptable solvates, together with pharmaceutically acceptable excipients or carriers;

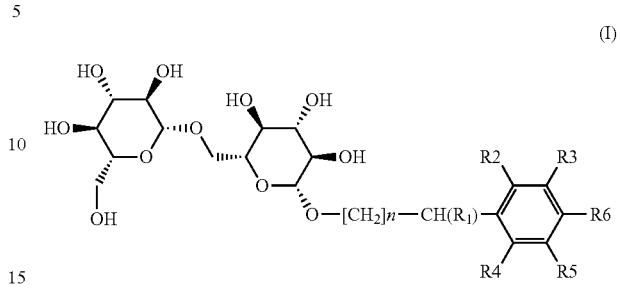

(I)

wherein n is an is an integer from 0 to 4; R1 is a radical selected from the group consisting of H, $CH_3$, $CH_2$-$CH_3$, $C(CH_3)_3$, COOH, $CONH_2$ and C≡CH; R2, R3, R4 [y] and R5 are radicals independently selected from the group consisting of H, F, Cl, Br, ($C_1$-$C_3$)-alkoxyl and ($C_1$-$C_4$)-alkyl; and R6 is a radical selected from the group consisting of H, F, Cl, Br, ($C_1$-$C_3$)-alkoxyl, ($C_1$-$C_4$)-alkyl, R7, CH=CH—R7 and O—$CH_2$—R7; and wherein R7 is phenyl or phenyl mono- or independently di-substituted with F, Cl, Br, ($C_1$-$C_3$)-alkoxyl or ($C_1$-$C_4$)-alkyl; and wherein the compound of formula (I) is selected from the group consisting of:

4-methoxybenzyl 6-O-(β-D-glucopyranosyl)-β-D-glucopyranoside;

(1RS)-1-phenylethyl-6-O-(β-D-glucopyranosyl)-β-D-glucopyranoside;

(1RS)-1-phenylpropyl-6-O-(β-D-glucopyranosyl)-β-D-glucopyranoside;

(1RS)-1-phenyl-2,2-dimethylpropyl-6-O-(β-D-glucopyranosyl)-β-D-glucopyranoside;

(2R)-2-[(6-O-(β-D-glucopyranosyl)-β-D-glucopyranosyloxy]phenylacetamide;

(1RS)-1-phenyl-2-propynyl-6-O-(β-D-glucopyranosyl)-β-D-glucopyranoside;

2-bromobenzyl-6-O-(β-D-glucopyranosyl)-β-D-glucopyranoside;

2-chlorobenzyl-6-O-(β-D-glucopyranosyl)-β-D-glucopyranoside;

2,4-dimethoxybenzyl 6-O-(β-D-glucopyranosyl)-β-D-glucopyranoside;

2-(2-cloro-6-fluorophenyl)ethyl 6-O-(β-D-glucopyranosyl)-β-D-glucopyranoside;

(Z)-4-stilbenemethyl [6-O-(β-D-glucopyranosyl)-D-glucopyranoside];

4-biphenylmethyl 6-O-(β-D-glucopyranosyl)-β-D-glucopyranoside;

4-ethoxybenzyl 6-O-(β-D-glucopyranosyl)-β-D-glucopyranoside;

4-t-butylbenzyl 6-O-(β-D-glucopyranosyl)-β-D-glucopyranoside; and 2-phenylethyl 6-O-(β-D-glucopyranosyl)-β-D-glucopyranoside.

* * * * *